（12) United States Patent
Zimmermann et al.

(10) Patent No.: US 10,488,400 B2
(45) Date of Patent: Nov. 26, 2019

(54) METHOD AND DEVICE FOR OPTICAL DETECTION OF A MOVEMENT IN A BIOLOGICAL SAMPLE WITH A SPATIAL EXTENT

(71) Applicants: Fraunhofer-Gesellschaft zur Foerderung der angewandten Forschung e. V., Munich (DE); Universitaet des Saarlandes, Saarbruecken (DE)

(72) Inventors: Heiko Zimmermann, Waldbrunn (DE); Frank Stracke, Saarbruecken (DE); Ronan Le Harzic, Woustviller (FR)

(73) Assignees: Fraunhofer-Gesellschaft zur Foerderung der angewandten Forschung e. V., Munich (DE); Universitaet des Saarlandes, Saarbruecken (DE)

( * ) Notice: Subject to any disclaimer, the term of this patent is extended or adjusted under 35 U.S.C. 154(b) by 0 days.

(21) Appl. No.: 15/555,773

(22) PCT Filed: Mar. 2, 2016

(86) PCT No.: PCT/EP2016/000377
§ 371 (c)(1),
(2) Date: Sep. 5, 2017

(87) PCT Pub. No.: WO2016/142043
PCT Pub. Date: Sep. 15, 2016

(65) Prior Publication Data
US 2018/0038845 A1 Feb. 8, 2018

(30) Foreign Application Priority Data

Mar. 6, 2015 (DE) .................. 10 2015 003 019

(51) Int. Cl.
*G01N 33/50* (2006.01)
*G01P 13/00* (2006.01)
(Continued)

(52) U.S. Cl.
CPC ......... *G01N 33/5005* (2013.01); *G01N 21/21* (2013.01); *G01N 33/15* (2013.01); *G01P 13/00* (2013.01)

(58) Field of Classification Search
CPC .............. G01N 33/5055; G01N 33/15; G01N 21/4788; G01N 21/49; G01N 2021/479; G01N 2021/4792; G01P 13/00
See application file for complete search history.

(56) References Cited

U.S. PATENT DOCUMENTS

| 4,411,525 | A | 10/1983 | Ogawa |
| 5,061,075 | A | 10/1991 | Alfano et al. |

(Continued)

FOREIGN PATENT DOCUMENTS

| CN | 101226158 A | 7/2008 |
| CN | 201311392 Y | 9/2009 |

(Continued)

OTHER PUBLICATIONS

Pomarico, J. A., and H. O. DiRocco. "Compact device for assessment of microorganism motility." Review of scientific instruments 75.11 (2004): 4727-4731 (Year: 2004).*

(Continued)

*Primary Examiner* — Dominic J Bologna
(74) *Attorney, Agent, or Firm* — Caesar Rivise, PC

(57) ABSTRACT

The invention relates to a method and a device for optical in vitro detection of a movement in a biological sample with a spatial extent in the form of a three-dimensional cell and/or tissue culture or a cell cluster or a sample made of freely swimming microorganisms. The method comprises the fol- (Continued)

lowing steps: (a) providing a receptacle for the sample (1), a light beam source (6), an optical unit (7, 8) and a detector (2), (a1) wherein the optical unit (7, 8) is embodied to illuminate the whole sample (1) in the receptacle with radiation emanating from the light beam source and to guide at least some of the radiation (11) of the light beam source (6), which is changed at any point within the sample (1) by an interaction with the sample (1) in terms of the beam direction thereof, the polarization state thereof and/or the diffraction pattern thereof, to a detection surface (2a) of the detector (2), and (a2) wherein the detector (2) is embodied to generate a measurement signal (9) in a manner dependent on the detected radiation, the time profile of which measurement signal specifies a time profile of an intensity of the detected radiation (11) and/or from which the time profile of the intensity of the detected radiation (11) is derivable; (b) illuminating the sample (1) with radiation from the light beam source; and (c) detecting a movement in the biological sample (1) in a manner dependent on a temporal change in the measurement signal (9).

20 Claims, 13 Drawing Sheets

(51) Int. Cl.
  *G01N 21/21* (2006.01)
  *G01N 33/15* (2006.01)

(56) References Cited

U.S. PATENT DOCUMENTS

| | | | |
|---|---|---|---|
| 5,434,667 | A | 7/1995 | Hutchins et al. |
| 5,627,308 | A | 5/1997 | Dahneke |
| 6,096,510 | A | 8/2000 | Hochman |
| 6,100,976 | A | 8/2000 | Ackerson |
| 6,671,540 | B1 | 12/2003 | Hochman |
| 7,449,097 | B2 | 11/2008 | Sekiwa et al. |
| 8,821,799 | B2 | 9/2014 | Bassler et al. |
| 9,126,199 | B2 | 9/2015 | Moritz et al. |
| 2002/0040851 | A1 | 4/2002 | Mc.Neil-Watson et al. |
| 2006/0105357 | A1* | 5/2006 | Benesch .............. B01L 3/5085 435/6.16 |
| 2012/0152745 | A1 | 6/2012 | Corbett et al. |
| 2013/0107276 | A1 | 5/2013 | Schussler et al. |
| 2015/0369790 | A1 | 12/2015 | Iwai et al. |
| 2016/0146732 | A1 | 5/2016 | Freitag et al. |

FOREIGN PATENT DOCUMENTS

| | | |
|---|---|---|
| CN | 102341694 A | 2/2012 |
| DE | 2904787 A1 | 8/1979 |
| DE | 7836339 U1 | 7/1981 |
| DE | 4215908 A1 | 11/1993 |
| DE | 68924749 T2 | 7/1996 |
| DE | 19836183 A1 | 3/1999 |
| DE | 102004009021 A1 | 11/2004 |
| DE | 102006003877 B4 | 10/2007 |
| DE | 102012016122 A1 | 2/2014 |
| DE | 202014004218 U1 | 5/2014 |
| DE | 112012004591 T5 | 9/2014 |
| DE | 102013211885 A1 | 12/2014 |
| EP | 0881490 A2 | 12/1998 |
| EP | 2342317 B1 | 12/2012 |
| EP | 2589924 A1 | 5/2013 |
| EP | 2955505 A1 | 12/2015 |
| JP | 62209338 A | 9/1987 |
| WO | 0216936 A1 | 2/2008 |
| WO | 2014123156 A1 | 8/2014 |

OTHER PUBLICATIONS

Cole, J. A., and M. H. Tinker. "Laser speckle spectroscopy—a new method for using small swimming organisms as biomonitors." Bioimaging 4.4 (1996): 243-253 (Year: 1996).*
English language machine translation of claims from DE 2904787 A1 (1979).
English language abstract for DE 4215908 A1 (1993).
English language machine translation of claims from DE 7836339 U1 (1981).
English language abstract for DE 19836183 A1 (1999).
English language abstract for DE 68924749 T2 (1996).
English language abstract for DE 102006003877 B4 (2007).
English language abstract for DE 102012016122 A1 (2014).
English language abstract for DE 102013211885 A1 (2014).
English language abstract for DE 112012004591 T5 (2014).
English language abstract for DE 202014004218 U1 (2014).
English language abstract for EP 0881490 A2 (1998).
English language abstract for EP 2589924 A1 (2013).
Baylor et al. (1977). A large birefringence signal preceding contraction in single twitch fibres of the frog. The Journal of physiology, 264(1), 141-162.
Cole et al. (1996). Laser speckle spectroscopy—a new method for using small swimming organisms as biomonitors. Bioimaging, 4(4), 243-253.
De Tombe et al. (1990). Force and velocity of sarcomere shortening in trabeculae from rat heart. Effects of temperature. Circulation research, 66(5), 1239-1254.
Noda et al. (2008). A new microscope optics for laser dark-field illumination applied to high precision two dimensional measurement of specimen displacement. Review of Scientific Instruments, 79(2), 023704:1-7.
Pomarico et al. (2004). Compact device for assessment of microorganism motility. Review of scientific instruments, 75(11), 4727-4731.
International Search Report from corresponding PCT/EP2016/000377 dated Jun. 14, 2016.
English Abstract for CN 101226158 A (2008).
English Abstract for CN 102341694 A (2012).
English Abstract for CN 201311392 Y (2009).
English Translation of Office Action dated Jul. 26, 2019 for CN App. No. 201680014161.3.

* cited by examiner

METHOD AND DEVICE FOR OPTICAL DETECTION OF A MOVEMENT IN A BIOLOGICAL SAMPLE WITH A SPATIAL EXTENT

CROSS-REFERENCE TO RELATED APPLICATIONS

This application is a U.S. National Phase Application of PCT/EP2016/000377, filed Mar. 2, 2016, which claims priority to DE 10 2015 003 019.1, filed Mar. 6, 2015, the contents of which applications are incorporated herein by reference in their entireties for all purposes.

BACKGROUND OF THE INVENTION

The invention relates to a method and a device for optical in vitro detection of a movement in a biological sample with a spatial extent.

It is known from practice that a requirement for monitoring the active dynamics of closed and three-dimensional cell and tissue cultures in areas such as development biology, toxicity testing and pharmaceutical research exists.

Tissue samples bred from embryonic stem cells that have differentiated into muscle tissue are for example used as part of toxicity tests in order to check the harmfulness of a substance to be tested. It is investigated here whether a substance applied to the muscle tissue influences the muscle contraction of the muscle tissue, which can be an indicator for the toxicity of the substance. Measuring methods are required for this in order to detect a movement, for example a contraction, in such a three-dimensional biological sample in the form of a cell cluster. Typical diameters of such cell clusters are 100 to 400 µm, whilst diameters within the millimeter range are also possible.

These studies are currently carried out mainly using visual observation and more rarely by using video microscopy with subsequent image analysis. The first is time consuming and is always connected with subjective assessment. The latter has the disadvantage that complex imaging optics and a complex image analysis connected with substantial research effort are required. Their inherent sensitivity towards small displacements is a further disadvantage.

Non-optical methods such as impedance measurements work only in contact with the sample. If the sample form does however deviate from the level (adherent monolayer) or is even three-dimensional, and also swims freely in a medium, the above mentioned techniques cannot be applied.

Automated imaging methods have the disadvantage that 10 to 40 image levels of the sample must for example be measured for a focal depth of 10 µm and the above mentioned typical size of the cell cluster of 100 to 400 µm. Given a typical minimum measuring period of approx. 10 seconds for being able to detect a movement and the additional time required for re-positioning or focusing, such methods are not suitable for quickly monitoring a multitude of samples.

A serial measurement of large numbers of samples is generally not indicated in view of the rather long monitoring period due to the time scales of biological dynamics. In practice, there is however a need to carry out such movement detection for a multitude of samples that are separate from each other, for example stored in a multi-well plate, also known as a micro-titer plate, for example with 96 or 384 cavities (English: wells). Imaging methods are not suitable for a parallel measurement of a multitude of such samples, as it is difficult to realize an arrangement of an imaging optical device at every cavity of the multi-well plate for geometric reasons and a lack of construction space.

It is therefore an objective of the invention to provide an improved method for detecting a movement in a biological sample with a spatial extent, with which the disadvantages of conventional techniques can be avoided. The invention is in particular based on the objective of providing a robust, contactless method for movement detection that requires no complex image analysis. It is a further objective of the invention to provide a method that is suitable for the parallel analysis of a multitude of samples in a screening environment. A further objective consists of providing a device for the detection of a movement in a biological sample with a spatial extent, with which disadvantages of conventional devices can be avoided.

These objectives are solved by devices and methods of the invention. Advantageous embodiments and applications of the invention. Advantageous embodiments and applications of the invention will be explained in more detail in the following description with partial reference to the Figures.

BRIEF SUMMARY OF THE INVENTION

The invention is based on the technical insight that optical methods are the most suitable for contactless monitoring and that it is necessary to illuminate the entire sample, as the precise location of a possible movement in a sample is not known in advance. As the sample normally has a substantial extent in depth, i.e. greater than the focal depth of imaging optics, interactions of the light with the sample must be cumulatively measured through the sample along its entire length. Transmission methods are therefore unsuitable, as the non-interactive part of the light in particular would be measured here and the fluctuations to be expected be accompanied by high background noise and interference, which would make this technique insensitive. The approach according to the invention is therefore based on the detection of the scattered radiation, polarization radiation and/or diffraction radiation of the illuminated sample, wherein the fluctuation caused by the sample movement is searched for in the part of the light that is changed by the interaction with the sample in its radiation direction, its polarization state and/or its diffraction pattern. It is of advantage here to separate the transmitting light from the scattered, polarization and/or diffraction radiation by means of suitable filters. The term "light" is also used in place of the term "radiation" as part of the present invention. Both terms can be considered equal as part of the present invention and comprise electromagnetic radiation within the visible, IR and UV range.

According to general aspects of the invention the same therefore provides a method for the optical in vitro detection of a movement in a biological sample with a spatial extent.

The method according to the invention comprises the provision of a receptacle for the sample, a light beam source, optics and a detector. The optics is here configured to illuminate the entire sample in the receptacle with radiation emanating from the light beam source and to guide at least part of the radiation of the light beam source, which is changed at any point inside the sample through interaction with the sample in its radiation direction, its polarization state and/or its diffraction pattern, onto a detector surface of the detector, so that the interactions of the radiation emanating from the light beam source with the sample is measured cumulatively along its entire path through the sample. The detector is configured to generate a measuring signal depending on the radiation detected, the time profile of which represents a time profile of the intensity of the detected radiation and/or from which the time profile of the intensity of the detected radiation can be derived.

The method according to the invention further comprises the illuminating of the sample with radiation from the light beam source and the detection of a movement in the biological sample depending on a temporal change of the measurement signal.

One particular advantage of the approach according to the invention is that the sample dynamics can be derived directly from the measured value of the method, as the fluctuations caused by a sample movement in the part of the light that has been changed in its radiation direction, polarization state and/or diffraction pattern through interaction with the sample are directly visible as fluctuations in the measurement signal. A complex processing of measurement data, as required with imaging methods, can thus be omitted.

The method can for example be designed to detect a movement in the sample if a change in the measurement signal exceeds a pre-determined threshold value. A movement can further be detected when checking contradictions in a muscle tissue if the temporal change of the measurement signal has periodicity.

The method may be carried out using comparatively simple optical elements. Optics for focusing on individual image levels and for the successive scanning of the sample volume is not required. The device for carrying out the method can therefore be realized cost effectively and be of a compact construction.

Thanks to the simple evaluation of the measurement signal and the compact construction the method is also suitable for the parallel monitoring of a multitude of samples and may be integrated into screening environments or into automated high-throughput processes, for example high-throughput screening processes, in a process-efficient way.

According to a particularly preferred embodiment the detector is provided as a single channel detector or the detector issues a single-channel measurement signal. The measurement signal preferably indicates only the radiation intensity impacting on the detector surface per time unit. A movement in the sample can therefore be detected directly by means of a temporal change or fluctuation of the signal.

The detector is preferably a non-imaging detector or a detector with a non-spatially resolved measurement signal, for example a non-spatially resolved photo detector, for example a photodiode. Such detectors are compact and cost effective.

A biological sample with a spatial extent is understood as a three-dimensional biological sample, for example in the form of a three-dimensional cell and/or tissue culture or a cell cluster.

The diameter of the biological sample may be at least 50 micrometers (μm) in at least one spatial direction, more preferably at least 50 micrometers in all spatial directions, and is often more than 100 μm in all spatial directions.

The diameter of the sample preferably lies within a range of 100 μm to 5 mm, more preferably within a range of 100 μm to 1 mm. The biological sample may in particular be a sample of muscle tissue and/or of living cells, i.e. of cells that have active dynamics, i.e. cells that can trigger a movement.

Detection of a movement in the biological sample should in particular be understood as a movement within the sample or a movement of a sample component of the biological sample. In other words, dynamic phenomena in or within biological samples with a spatial extent should in general be detectable. With cell cultures of muscle cells such movements can for example be triggered by a contraction of individual muscle cells.

The biological sample may however also be a sample of freely swimming microorganisms, for example spermatozoa. In this case the method for detection of movement of the freely swimming microorganisms can be used, for example in the case of spermatozoa, for determining sperm motility.

The optics may comprise illumination optics arranged on the illumination side, with which the radiation of the light beam source is directed at the whole sample in order to illuminate the sample completely and as evenly as possible.

The optics may also comprise detection optics, with which the light emanating from the sample, the radiation direction, polarization state and/or diffraction pattern of which is changed by an interaction with the sample, is directed at a detection surface of the detector.

This functional characteristic of the optics may be realized using one or more expediently arranged and designed known optical construction elements such as for example filters, lenses, apertures, refractive elements etc. here, as will be explained hereafter with reference to further embodiment examples.

One advantageous embodiment variant envisages here that the optics is configured and/or the detector is arranged relative to the illumination beam path and the sample in such a way that no beam paths exist where transmitting radiation of the light beam source transmitted through the sample reaches the detector and/or where light from the light beam source reaches the detector whilst bypassing the sample.

According to this embodiment only the light from the light beam source that has been changed in its radiation direction, its polarization state and/or diffraction pattern through an interaction with the sample therefore reaches the detector, whilst the optics prevents that transmitting radiation or radiation bypassing the sample reaches the detection surface of the detector. In this way interfering background signals are reduced and the sensitivity of the measurement is increased.

According to a preferred embodiment a movement in the sample is recognized by means of a change in the diffraction pattern. According to this embodiment the light beam source generates coherent light. The optics is also configured, for example by means of a spatial filter, to map an edge area of a diffraction pattern created by light from the light beam source diffracted by the sample, on the detector. A movement within the sample generates a change in the diffraction pattern, for example a speckle pattern. Investigations carried out as part of the invention have shown that a change in the diffraction pattern is difficult to measure in its center, as the relative change in radiation intensity is small. In the edge area, the change can however be recognized reliably and can for example lead to a temporary change from a local diffraction maximum to a local diffraction minimum or vice versa in the diffraction pattern. With a diffraction pattern, each point in the pattern contains the diffraction information of the entire sample.

With one advantageous variant of this embodiment the optics comprises a pinhole aperture, which is arranged between the sample and the detector in such a way that a pinhole of the pinhole aperture is arranged in the edge area of the diffraction pattern generated by the sample.

A pinhole aperture is understood as a hole-shaped opening, preferably a small hole-shaped opening, and preferably without a lens. Pinhole apertures serve for the locally delimited collection of light. The front sides of optical fibers have long been used for the same purpose, in particular in confocal microscopes.

All observation angles in which no transmitted light is received should preferably be regarded as the edge area of the diffraction pattern. The diffraction pattern is caused by the positive and negative interference of light waves diffracted on objects, here the sample. It will depend on the object size, wave length of the light and the observation angle whether interference is positive or negative. Light that passes through the sample without interaction, i.e. transmitted light, ballistic photons, has an observation angle of 0° and arrives in the middle of the diffraction pattern. The diffraction pattern is outshone by the transmitted light and the S/B (S/B: signal-to-background, signal background) ratio and the S/N (S/N: signal-to-noise, signal noise) ratio fall drastically. All observation angles at which no transmitted light is received should therefore preferably be considered to represent the edge area of the diffraction pattern. As the entire sample is here irradiated and illumination is not collimated, the "receiving area" of the transmitted radiation is greater than just one point.

According to a further variant of this embodiment the pinhole aperture may have several pinholes arranged relative to the diffraction pattern in such a way that they are located in an edge area of the diffraction pattern. For this the pinholes should be arranged in such a way that an overlaying of the diffraction radiation which impacts upon the detector through the pinholes will increase rather than worsen the diffraction effect.

According to a further variant of the embodiment, which detects a movement in the sample by means of a change in the diffraction pattern, the optics may comprise an aperture between the light beam source and the sample, which is configured in such a way that radiation from the light beam source, exiting through an aperture opening of the aperture, does not impact upon the pinhole in the pinhole aperture directly, i.e. bypasses the sample. The optics may further comprise a refractive optical element, i.e. an element that refracts the radiation, for example a convex lens or a prism, arranged between the light beam source and the sample, which is configured in such a way that radiation deflected by the refractive element does not impact upon the pinhole in the pinhole aperture directly, i.e. by bypassing the sample. These variants represent a cost effective example of an optics that is easy to adjust and guides only diffracted radiation to the pinhole of the pinhole aperture.

According to a further preferred embodiment a movement in the sample is detected by means of a fluctuation in polarized light caused by the movement. According to this embodiment the optics comprises a first polarization filter and a second polarization filter, which have different polarization directions, wherein the first polarization filter is arranged between the light beam source and the sample, and the second polarization filter between sample and detector. A movement in the sample leads to a changed interaction between the polarized light with the sample and to a change in the polarization states, which leads to fluctuation in the detector signal.

The detector and the second polarization filter may be arranged on the opposite side of the sample in relation to the light beam source, to the side of the sample or on the same side as the light beam source here.

According to a further preferred embodiment a movement in the sample is detected by means of fluctuation in the light scattered by the sample, and that is caused by the movement. The detector may be arranged on the same side of the sample (1) as the light beam source for the epidetection of light scattered by the sample here. Alternatively, the detector may be arranged at a tilt angle in relation to the direction of the illumination beam path and/or to the side of the sample for the detection of radiation scattered to the side of the sample.

These variants offer the advantage that no optical components, such as for example apertures are required that would prevent that transmission radiation impacts upon the detector.

The detector may further be arranged in a transmitted light direction to the sample for a transmitted light detection of light scattered by the sample. According to this variant the optics comprises an aperture arranged between the light beam source and the sample, configured to block light beams in the illumination beam path that would impact upon the detector as beams transmitted through the sample. Alternatively or in addition the optics may comprise a refractive optical element arranged between the light beam source and the sample, configured to change a direction of the illumination beam path in such a way that light beams transmitted through the sample do not impact upon the detector.

It is also of advantage if the optics has a bandpass filter arranged before the detector, which is designed for room light suppression. In this way, the sensitivity of the detection may be increased further.

According to a further preferred variant the optics, in particular the illumination optics, comprises an axicon. Use of an axicon offers the advantage of a more homogeneous illumination of spatially "deeper" samples compared to conventional lenses, as the focus of an axicon extends along the optical axis—instead of on just one point. A further advantage of an axicon is the easy spatial filtering of incoming (non-influenced) light, as this is diffracted with a constant angle to the optical axis.

One possibility of the realization according to the invention envisages that the sample may be located on a carrier matrix. The receptacle of the sample can therefore comprise a carrier matrix, preferably a biopolymer. The sample can also be located in a hanging drop. The receptacle of the sample can therefore comprise a hanging drop. The receptacle of the sample can further be designed as a carrier matrix located in a hanging drop, the carrier matrix being preferably a biopolymer such as for example alginate.

The receptacle for the sample may be a cavity of a multi-well plate (micro-titer plate) for using the method in a screening environment. The receptacle can also be a cavity of a multi-well plate designed for forming a hanging drop on the individual cavities (so-called hanging drop multi-well plate). Such hanging drop multi-well plates are for example offered by the company Insphero AG, CH-8952 Schlieren, under the name ""GravityPLUS™ 3d Culture and Assay Platform". Patent document EP 2342317 B1 also discloses such a plate.

It has already been mentioned above that the method is particularly suitable for the parallel monitoring of a multitude of samples, for example of samples to be examined as part of automated high-throughput methods.

One advantageous further development of the method therefore envisages that a parallel optical detection of a movement is carried out in several biological samples, which are separate from each other, with the same. The receptacle for the biological samples is preferably a multi-well plate here, which has a number of cavities arranged in rows and columns for receiving the samples. The detector is designed as a detector array, preferably as a photodiode array, wherein a grid distance of individual detectors equals a grid distance of the cavities of the multi-well plate.

The light beam source is configured to illuminate individual cavities. According to an advantageous variant the light beam source for illuminating the samples in the cavities is configured as a laser diode array, wherein a grid distance of individual laser diodes equals the grid distance of the cavities of the multi-well plate. A laser diode array represents a space saving and energy efficient illumination source.

In order to enable good heat dissipation, the bracket of the laser diode array may be made from a heat conducting material, preferably from aluminum. The optics according to this variant can also comprise a lens array, for example a micro-lens array, wherein each lens of the lens array is allocated to one of the laser diodes and the lenses guide the light of the laser diodes into the cavities.

The light beam source can also be designed as a conventional light source (laser, arc lamp etc.), as a light beam source instead of a laser diode array, wherein the light of the light beam source is coupled into the individual cavities containing the samples for illuminating the samples by means of an optic fiber bundle. Each optic fiber is allocated to a cavity here. This offers the advantage that the light source can be operated at sufficient distance from the sample to avoid excessive heat development near the sample.

According to a further alternative variant the possibility of surface illuminating the multi-well plate with a light beam source also exists, which represents a simple realization variant, but has energy efficiency disadvantages, as the light beam source must have a corresponding performance capacity. It is of advantage here if the light is guided via expediently designed condenser optics, and possibly angle-dependent pass-through filters parallelized and targeted at the cavities.

According to a further aspect of the invention a device for the contactless in vitro detection of a movement in a biological sample with a spatial extent is provided. The device comprises a receptacle for the biological sample, a light beam source, a detector and optics, configured to illuminate the whole sample in the receptacle with radiation emanating from the light beam source and to guide at least part of the radiation of the light beam source, which has been changed in its radiation direction, its polarization state and/or its diffraction pattern at any point within the sample through an interaction with the sample, onto a detector surface of the detector. The detector is configured to generate a measurement signal in dependence on the detected radiation, which represents the time profile of the intensity of the detected radiation and/or from which the time profile of the intensity of the detected radiation can be derived.

The device may also have an evaluation unit equipped for detecting a movement in the biological sample by displaying and/or evaluating a temporal change in the detected radiation.

Features disclosed purely as part of the method shall also be considered as disclosed and claimed for the device in order to avoid repetition. The above mentioned aspects and features of the invention, in particular with regard to the design of the optics, the detector, the receptacle, for example as a multi-well plate, hanging drop or hanging drop multi-well plate, and the light beam source therefore also apply for the device.

BRIEF DESCRIPTION OF THE DRAWINGS

The previously described preferred embodiments and characteristics of the invention may be combined with each other in any way. Further details and advantages of the invention will be described hereafter with reference to the enclosed drawings. Shown are.

DETAILED DESCRIPTION OF PREFERRED EMBODIMENTS

Identical parts are identified with the same reference numbers in the Figures and will not be described separately.

Figure 1:
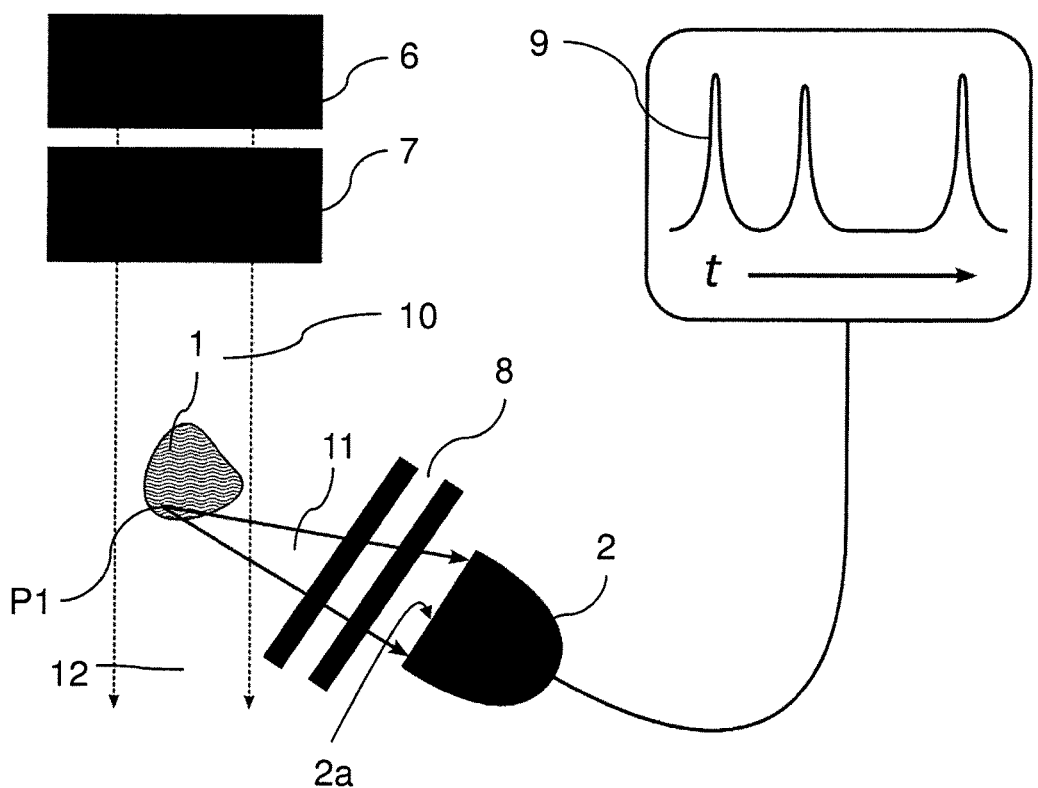
FIG. 1 a highly schematic illustration of a method and a device according to an embodiment of the invention.

FIG. 1 shows a highly schematic illustration of a method and a device according to an embodiment of the invention.

A device 100 for the optical in vitro detection of a movement in a biological sample 1 with a spatial extent is provided for carrying out the method.

The device 100 comprises a receptacle (not illustrated) for the three-dimensional sample 1, a light beam source 6, optics 7, 8 and a detector 2.

The receptacle is not limited to a specific type of receptacle, but may be expediently designed depending on the application and type of the sample, for example as a carrier, carrier plate, as a vessel, as a cavity of a multi-well plate or as a carrier matrix in the form of a biopolymer, for example as an alginate, on which the sample is grown.

The light source 6 can, but does not have to be a coherent light source, for example a laser. Only embodiment variants that use a diffraction pattern of the sample for movement detection (compare FIGS. 4A to 4C, 5A to 5C) require coherent radiation.

The illustration of the optics 7, 8 in FIG. 1 is merely schematic and is meant to illustrate the functional characteristic of the optics rather than illustrate specific optical elements, as a multitude of specific optical embodiment variants are possible in principle, of which some are described in the following Figures by way of example.

This functional characteristic of the optics may be realized using one or more expediently arranged and designed known optical construction elements and components such as for example filters, lenses, apertures, refractive elements etc. here.

The optics 7, 8 comprises illumination optics 7 arranged on the illumination side, with which the radiation 10 of the light beam source 6 is guided onto the whole sample 1 in order to illuminate the sample completely and as evenly as possible. The illumination optics may comprise suitable optical elements or components such as apertures, lenses and/or filters for forming radiation for this. The use of an axicon is particularly advantageous.

The optics 7, 8 further comprises detection optics 8, by means of which the light 11 emanating from the sample, i.e. light from the light beam source 6 that has been changed in its radiation direction, its polarization state and/or its diffraction pattern by an interaction with the sample 1, is guided onto a detection surface 2a of the detector 2. In FIG. 1 a scattering event is for example illustrated at point P1, where the light 11 is scattered in the direction of the detector 2 and mapped onto the detector 2 by means of the detection optics 8. As the whole sample 1 is illuminated evenly the interaction of incoming light 10 can take place at any point within the sample 1, so that the interactions of the light with the sample are measured across its entire path through the sample, in a cumulative manner by the detector 2.

The detection optics 8 can further include optical elements that ensure that light that has not been changed in its radiation direction, its polarization state and/or its diffraction pattern through an interaction with the sample will not reach the detector 2. The detection optics 8 can for example include a bandpass filter arranged before the detector inlet, which filters out or suppresses room light, but lets light with a wavelength of the light beam source 6 pass. This assumes that a monochromatic light beam source is used or that a corresponding filter is arranged at the outlet of the light beam source in order to illuminate the sample with a specific light wavelength only.

The detection optics 8 can also block beam paths by means of apertures, lenses etc., where transmitting radiation from the light beam source 6 transmitted by the sample 1 would reach the detector and/or where light from the light beam source 6 would reach the detector 2 whilst bypassing the sample.

In addition or alternatively the detector may also be arranged in such a way that no transmitted light 12 reaches its detector surface 2a, for example by arranging the detector 2 on the side relative to the illumination beam path 10, as illustrated in FIG. 1.

The detector 2 is configured to generate a measurement signal 9 depending on the detected radiation 11, the time profile of which specifies a time profile of an intensity of the detected radiation 11.

The detector signal 9 therefore equals a volume measurement (English: full-volume measurement) of the sample. The detector 2 is preferably a single-channel detector, so that only one measurement parameter 9, which equals the fluctuation of the light intensity recorded by the detector per time unit, is generated. The detector 2 is for example a conventional photodiode 2.

The sample 1 is illuminated with the device 100 illustrated in FIG. 1 and the corresponding measurement signal 9 evaluated.

If a movement now occurs in the sample 1, for example a contraction in the case of cultivated muscle tissue, then the interaction of the sample 1 with the light reaching the sample will also be changed by the movement, i.e. the proportion of light 11 falling onto the sample that is changed in its radiation direction, its polarization state and/or its diffraction pattern through an interaction with the sample 1 will change and generates a change in the detector signal 9. According to the method a movement in the biological sample can therefore be detected by means of the fluctuation in the detector signal 9.

Some examples of embodiments of the invention will be described hereafter, which represent specific designs of the solution approach illustrated in FIG. 1. The light beam source 6 is not illustrated in FIGS. 2A to 3C, but is located above the optics and detector arrangement shown, which is clear from the beam path 10.

Figure 2A:
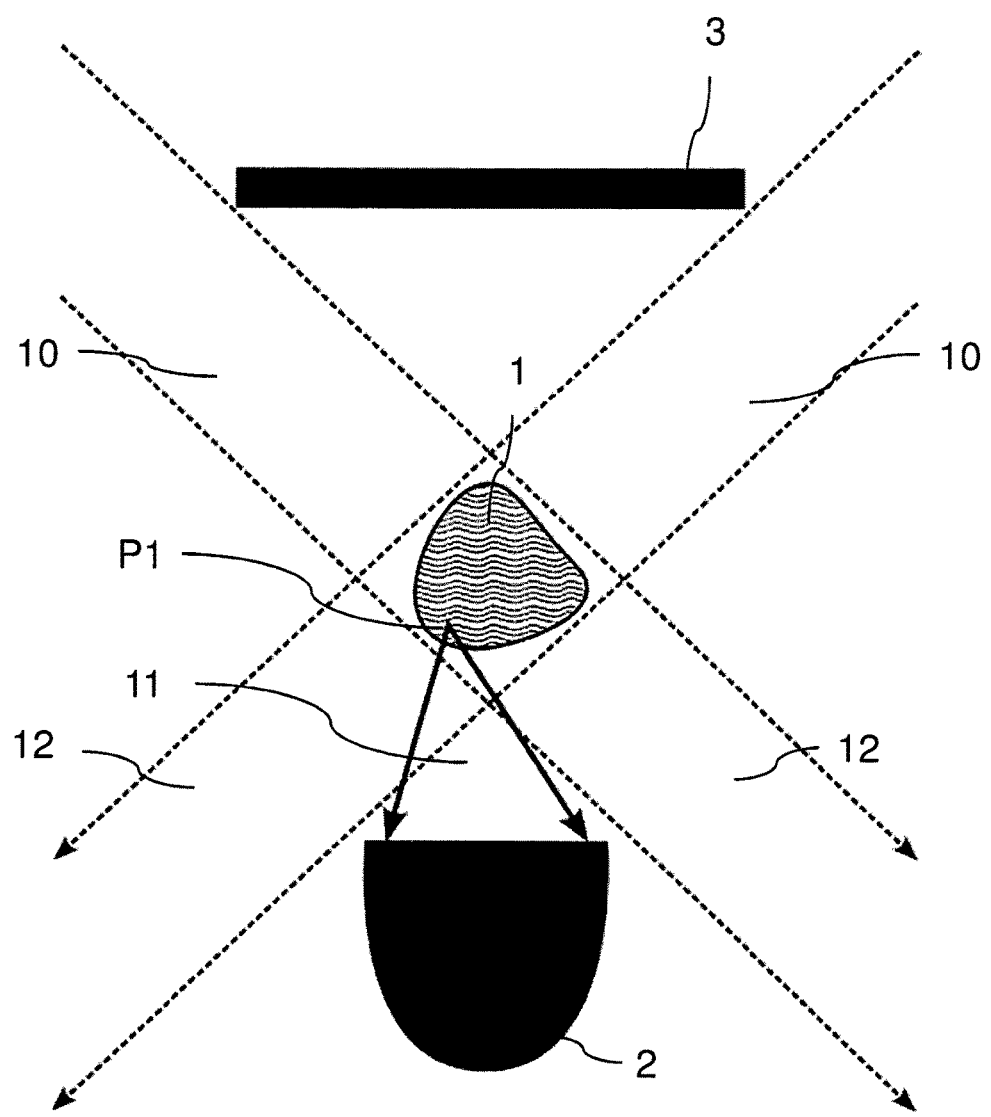
FIGS. 2A-2E embodiments of the invention using light scattered by the sample for movement detection.
Figure 2B:
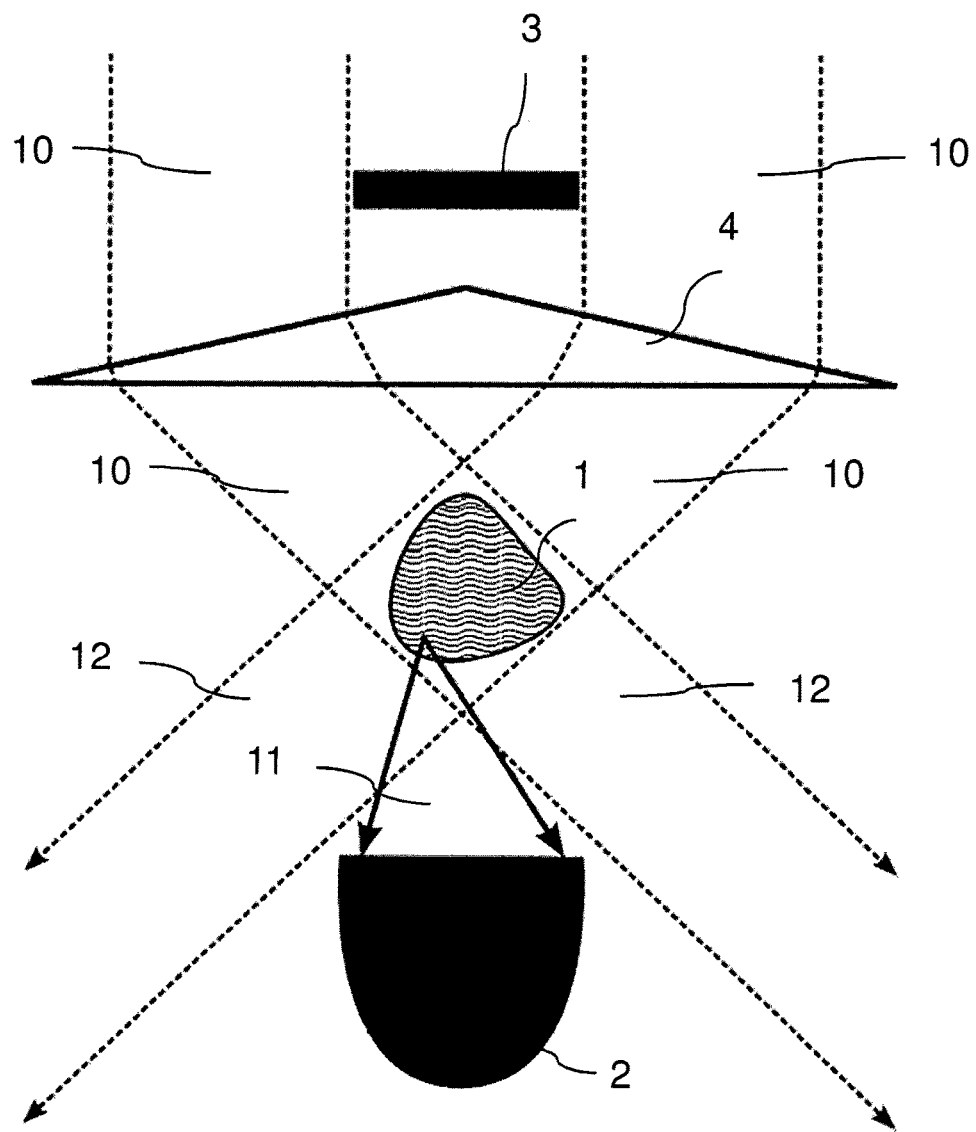

FIGS. 2A to 2E show embodiments of the invention that use light scattered by the sample for movement detection. In FIGS. 2A to 2B the detector 2 is arranged in transmitted light direction to the sample 1 for a transmitted light detection of the scattered light 11 of the sample 2. In order to prevent that beams transmitted through the sample 2 reach the detector 2 an aperture 3 that blocks light beams that would reach the detector 2 as beams transmitted through the sample 2, or which could pass by the side of the sample and reach the detector 2, is arranged in FIG. 2A. The illumination optics in the form of the aperture 3 therefore admits only radiation 12 transmitted through the sample that will not reach the detector 12.

The particularity of the embodiment illustrated in FIG. 2B is that a smaller aperture 3 is used instead of a large aperture 3, which is followed by a refractive optical element, for example a lens, an axicon etc., which changes the direction of the illumination beam path 10 admitted through the aperture 3 in such a way that beams 12 transmitted through the sample 2 cannot reach the detector 2.

Figure 2C:
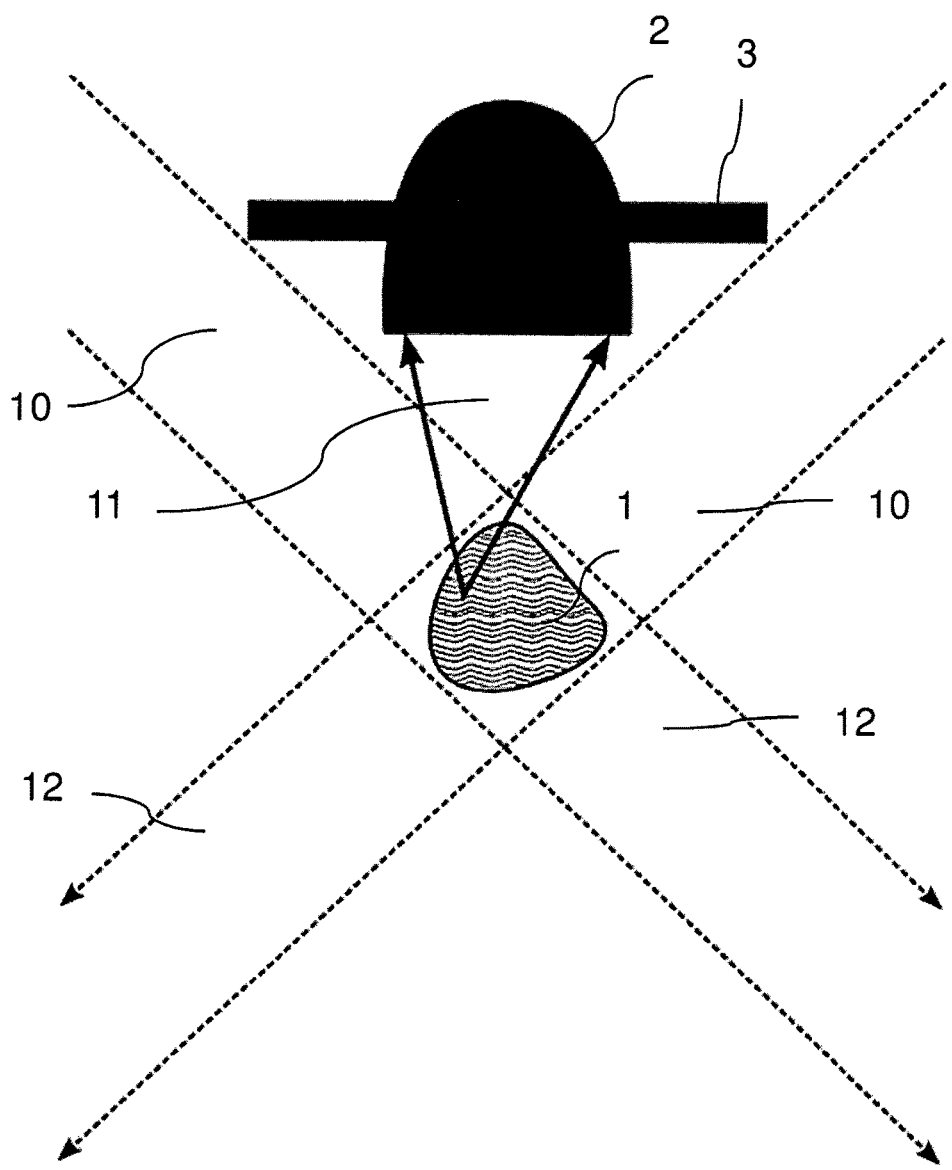

The particularity of the embodiment illustrated in FIG. 2C is that the detector 2 is arranged on the same side of the sample 1 as the light beam source 6 for the epidetection of scattered light in the form of reflection from the sample 1, wherein the detector surface 2a in turn faces the sample 2. This offers the advantage that no aperture for blocking transmitted light is required. Nevertheless, an aperture surrounding the detector 2 is envisaged here, which can reduce the influence of interfering light influence.

Figure 2D:
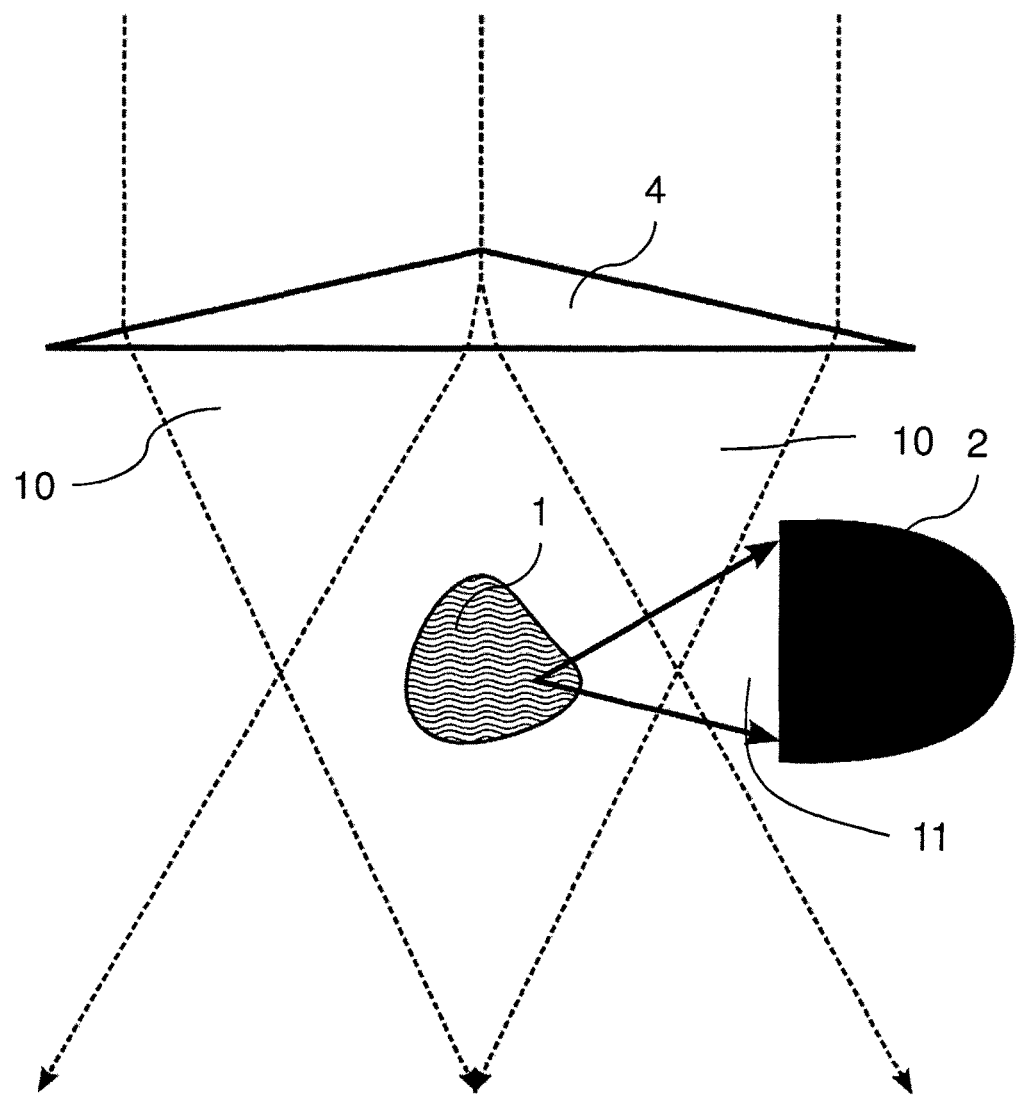
Figure 2E:
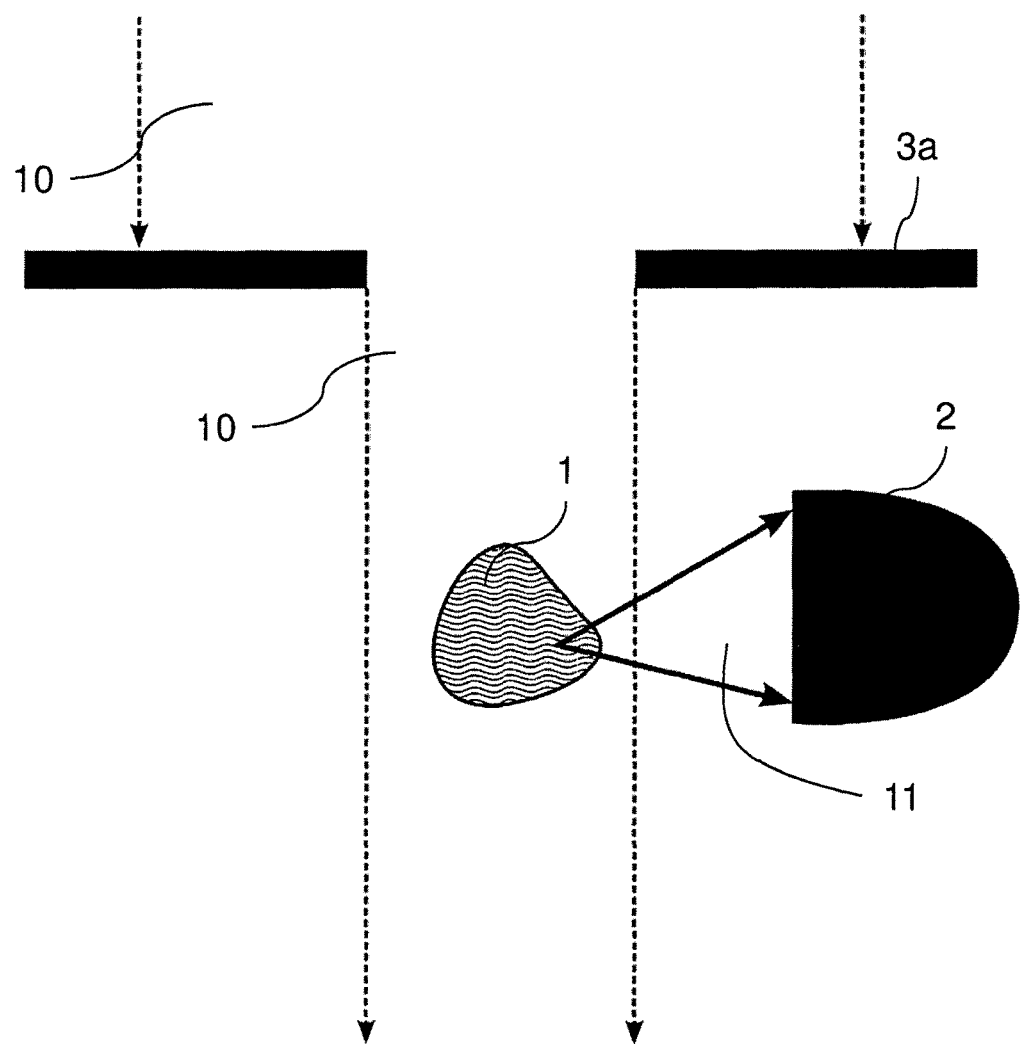

The particularity of the embodiment variants illustrated in FIGS. 2D and 2E is that scattered light 11 is detected at the side. For this the detector 2 is arranged to the side of the illumination direction. In FIG. 2D a refractive optical element, for example a lens or prism 4, is arranged between the light beam source and the sample 1, which changes the direction of the beam path in such a way that light of the illumination beam path 10 cannot reach the detector 2 directly, i.e. whilst bypassing the sample 1.

The embodiment illustrated in FIG. 2E differs from the variant in FIG. 2E in that an aperture 3a is used instead of the refractive optical element 4, which has an opening for narrowing the beam path 10, so that light of the illumination beam path 10 can once again not reach the detector 2 directly, i.e. whilst bypassing the sample 1.

Figure 3A:
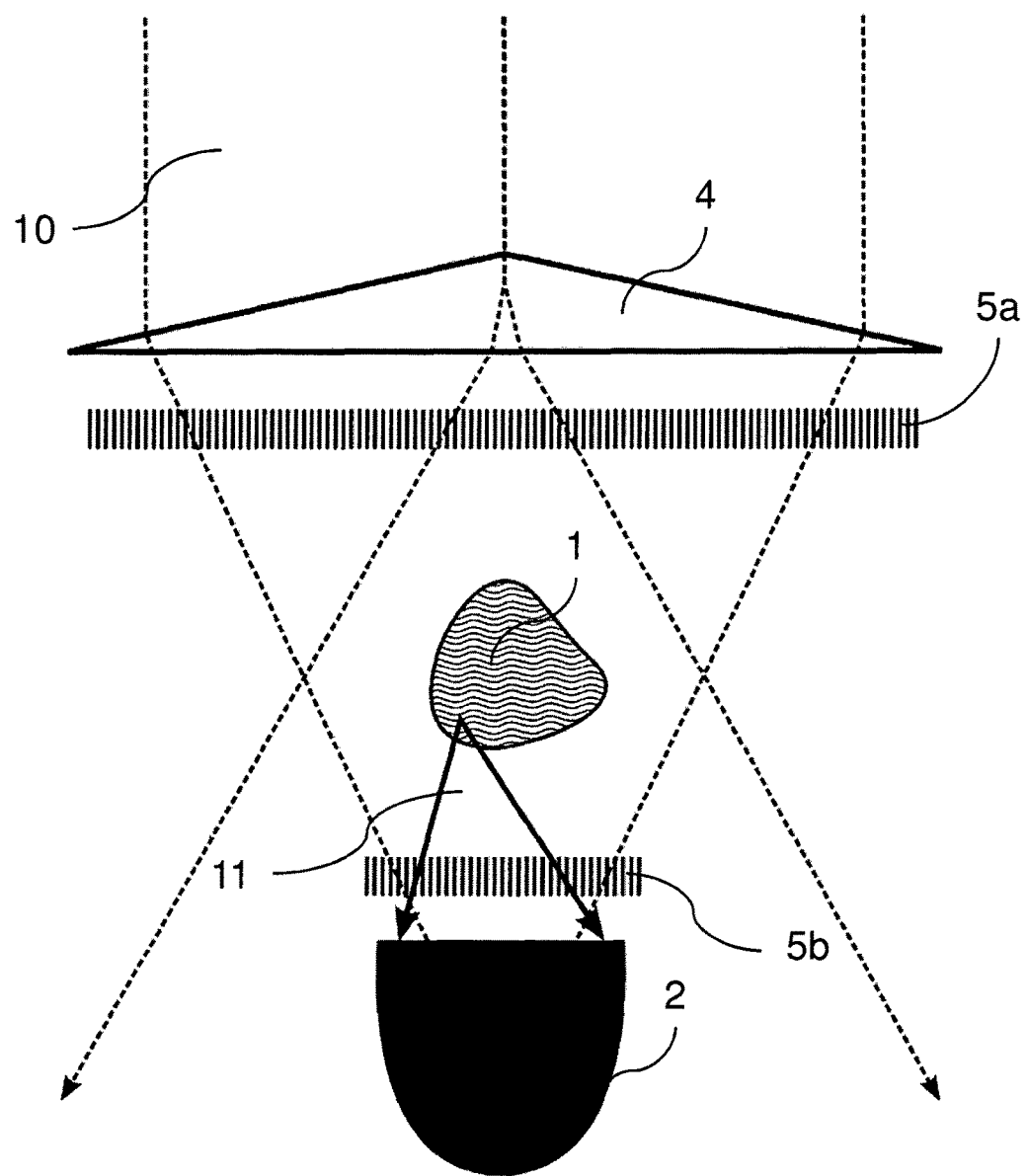
FIGS. 3A-3C embodiments of the invention using polarized light for movement detection.
Figure 3B:
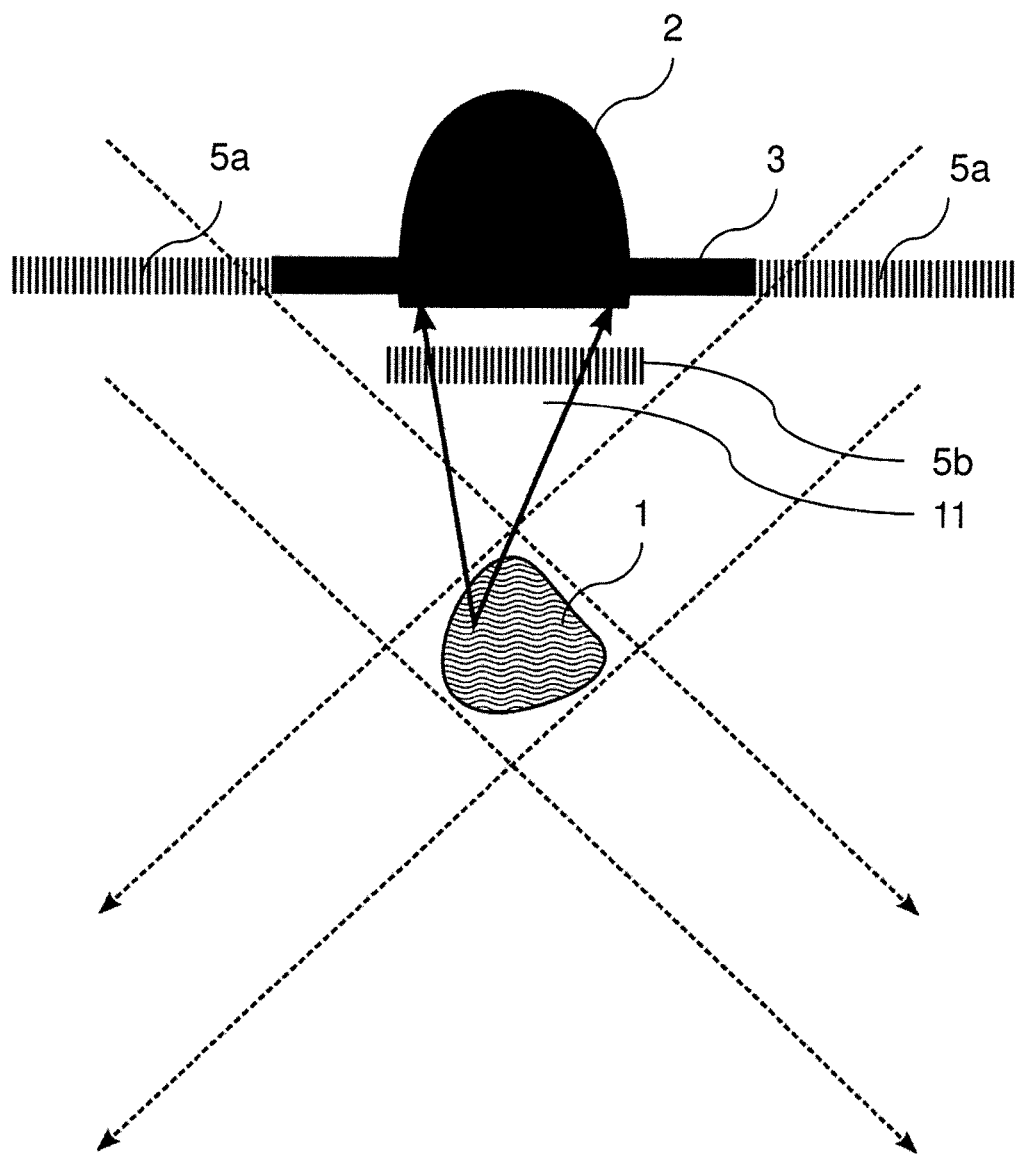
Figure 3C:
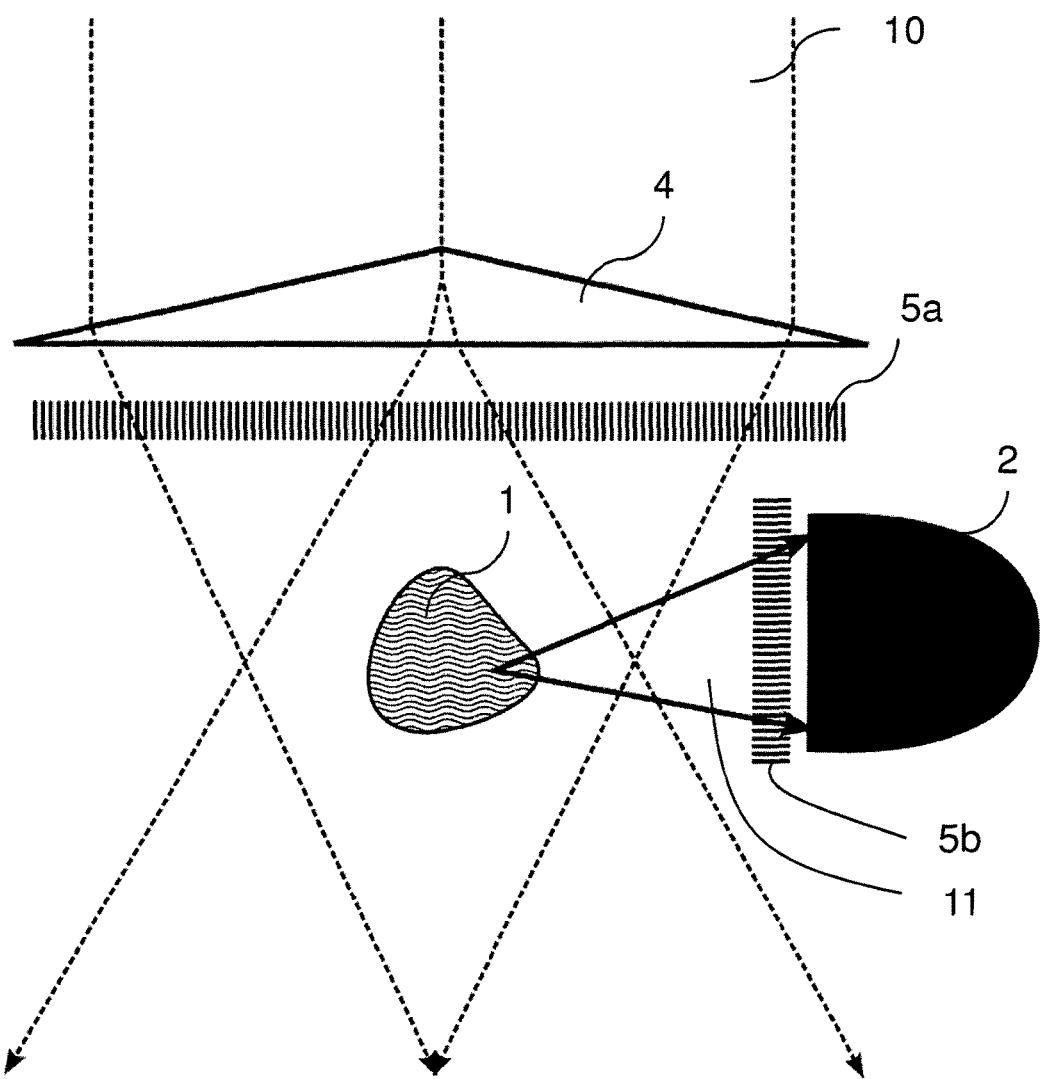

FIGS. 3A to 3C show embodiments of the invention using polarized light for movement detection. For this the illumination optics comprises a first polarization filter 5a, arranged between the light beam source and the sample 1. The detection optics comprise a second polarization filter 5b, which has a different polarization direction compared to the first polarization filter 5a and is arranged between the sample 1 and the detector 2, preferably at the detector inlet.

The detector 2 and the second polarization filter 5b may be arranged on the opposite side of the sample 1 with regard to the light beam source, to the side of the sample 1 or on the same side as the light beam source, which is illustrated by the different variants in FIGS. 3A to 3C.

Due to the different polarization directions of the two polarization filters 5a and 5b the polarization filter 5b lets only light that has been "depolarized" through interaction with the sample pass through. The arrangement of the two polarization filters 5a and 5b thus ensures that no light transmitted through the sample or light that has bypassed the sample is detected.

A movement in the sample will change the proportion of depolarized light and leads to a fluctuation in the detector signal, so that a movement in the sample 1 can in turn be detected directly from the fluctuation of the detector signal.

A refractive optical element 4, for example a convex lens or a prism that focuses the illumination beam path 10 on the sample, may be arranged before the first polarization filter 5a to reduce scattered light effects (FIGS. 3A and 3C).

In the embodiment of FIG. 3B the detector 2 is arranged on the same side of the sample 1 as the light beam source 6 for the epidetection of scattered light in the form of reflection from the sample 1. An aperture 3 surrounding the detector 2 may be envisaged here, which can reduce the influence of interfering light influences.

Figure 4A:
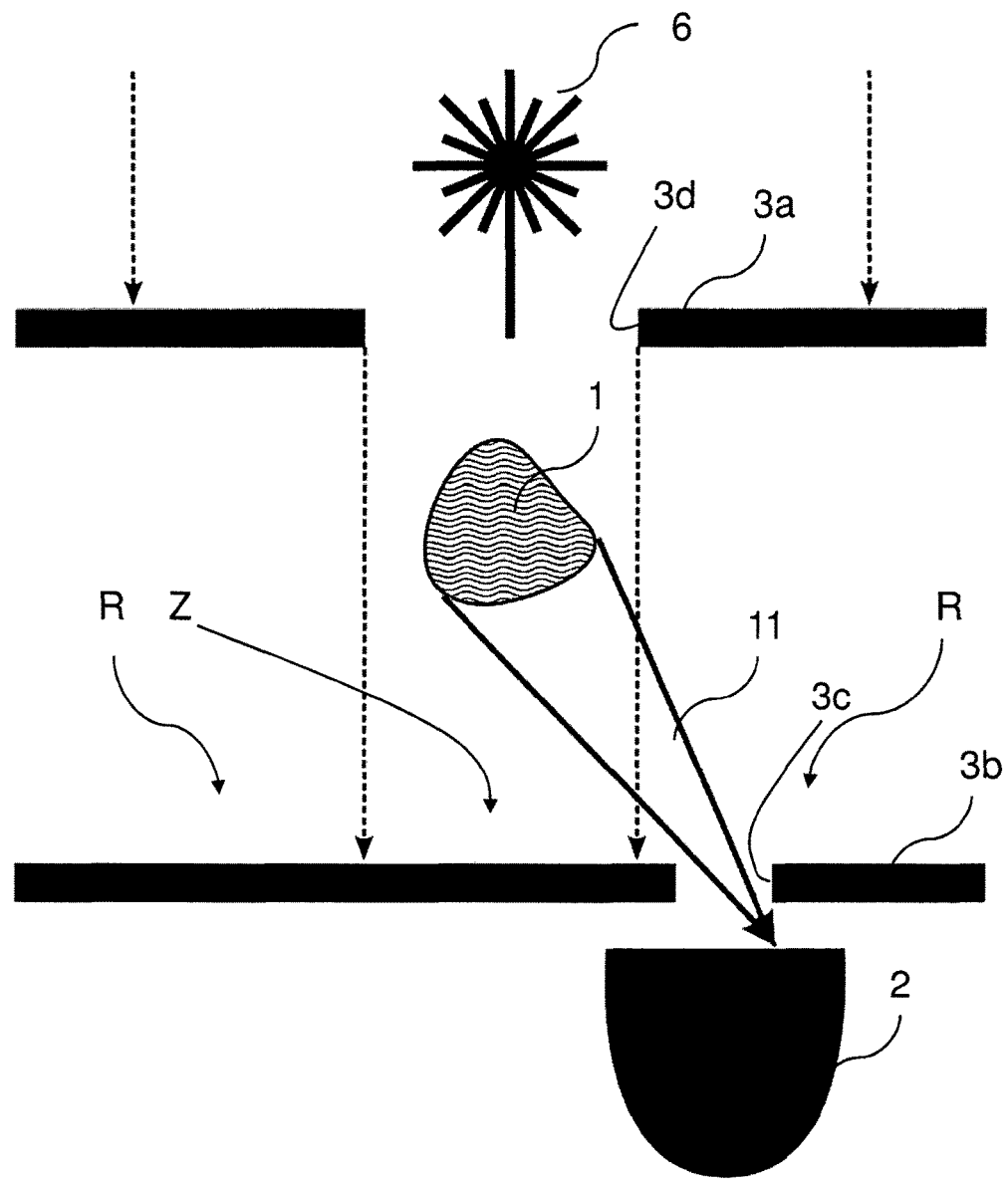
FIGS. 4A-4C embodiments of the invention using a diffraction pattern of the sample for movement detection.
Figure 4B:
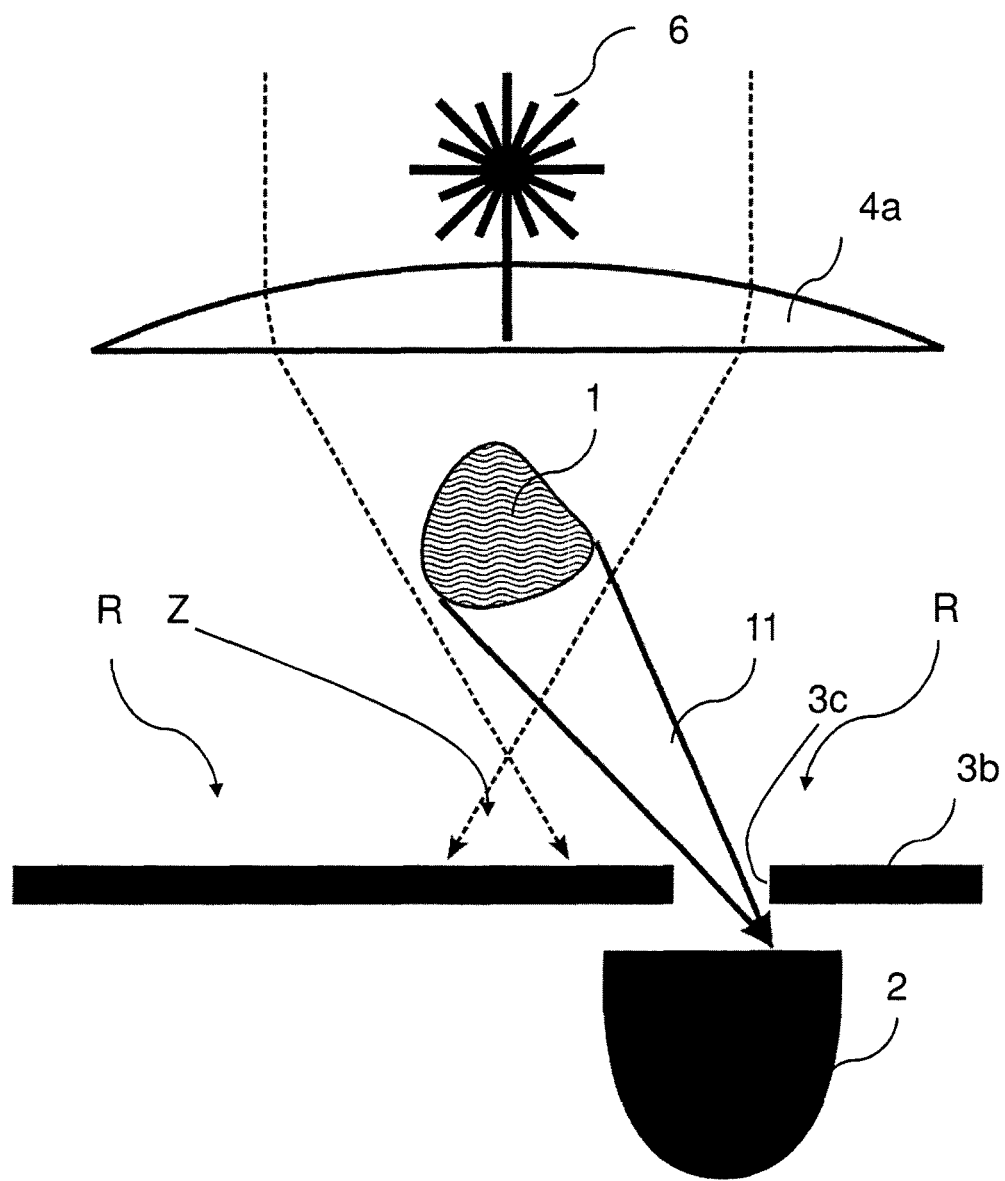
Figure 4C:
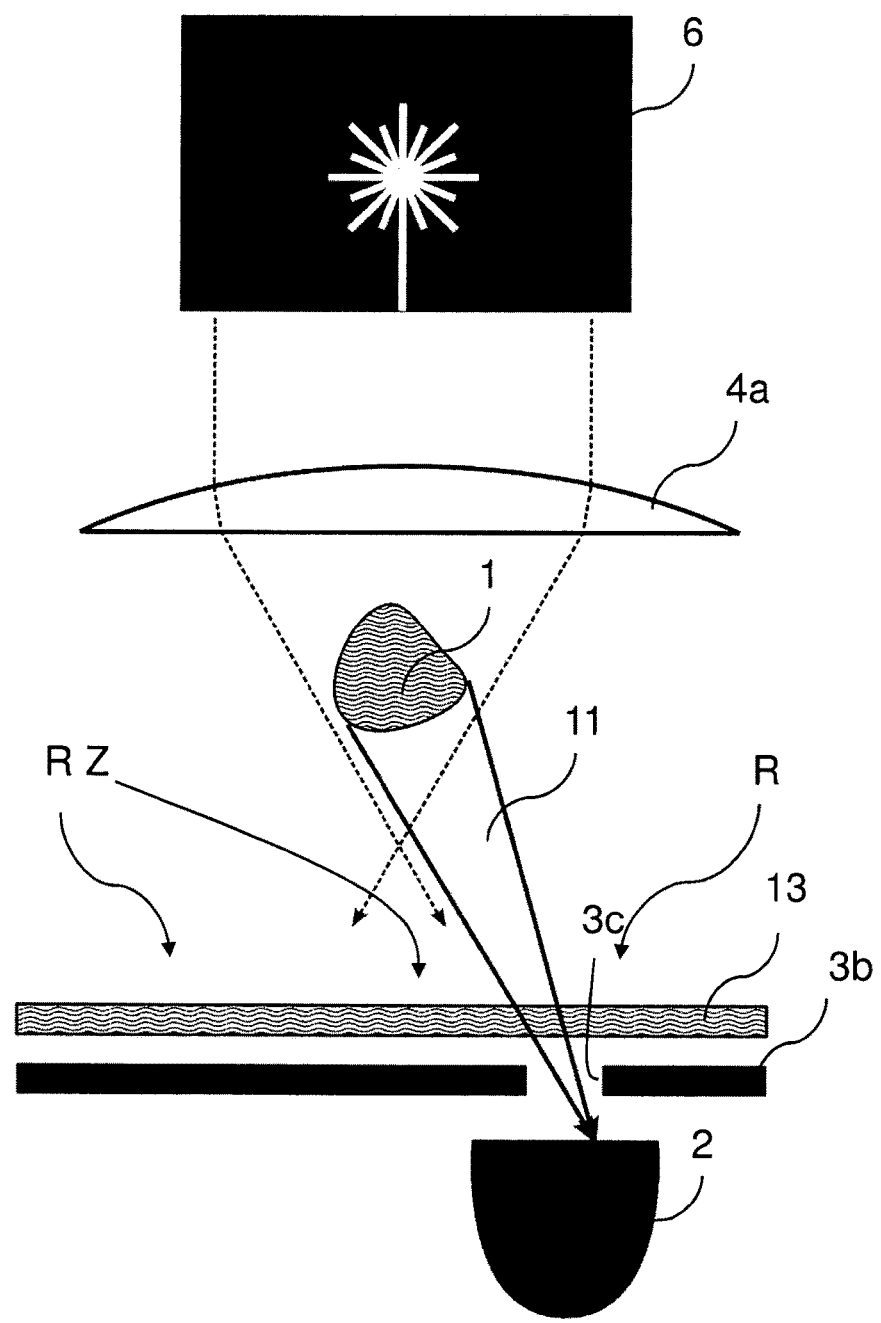

FIGS. 4A to 4C show embodiments of the invention using a diffraction pattern of the sample, for example in the form of a speckle pattern, for movement detection. The light source 6 is a coherent light source, for example a laser diode. Light of the light beam source 6 diffracted at the sample generates a diffraction pattern with a center Z of high intensity and an edge area R of low intensity.

The detection optics comprise a pinhole aperture 3b arranged in front of the detector 2, arranged between the sample 1 and the detector 2 in such a way that a pinhole 3c of the pinhole aperture 3b is arranged in the edge area R of the diffraction pattern generated by the sample.

According to the variant of FIG. 4A the illumination optics comprise an aperture 3a arranged between the light beam source and the sample, configured in such a way that radiation from the light beam source 6 exiting through an aperture opening 3d of the aperture 3a will not reach the pinholes 3c of the pinhole aperture 3b directly.

According to the variants of FIGS. 4B and 4C the illumination optics comprise a refractive optical element 4a, for example a concave lens, between the light beam source 6 and the sample 1, which is designed in such a way that radiation diffracted by the refractive optical element 4a will not reach the pinhole 3c of the pinhole aperture 3b directly, i.e. whilst bypassing the sample.

In the variant of FIG. 4C a bandpass filter 13 is also arranged between the sample 1 and the pinhole aperture 3b, which filters out room light that does not equal the wavelength of the light beam source 6. Heart muscle beats can currently be detected with a sensitivity comparable to visual observation (with a microscope) with the construction shown in FIG. 4C.

Figure 5A:
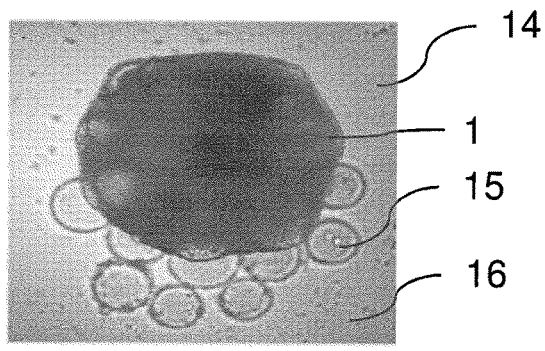
FIG. 5A a sample in the form of a heart muscle tissue model on a carrier matrix.
Figure 5B:
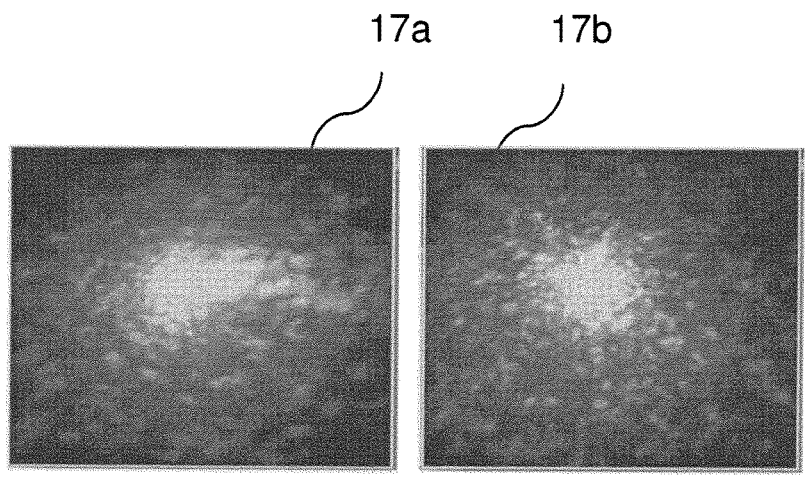
FIG. 5B illustration of a speckle pattern at two successive points in time.
Figure 5C:
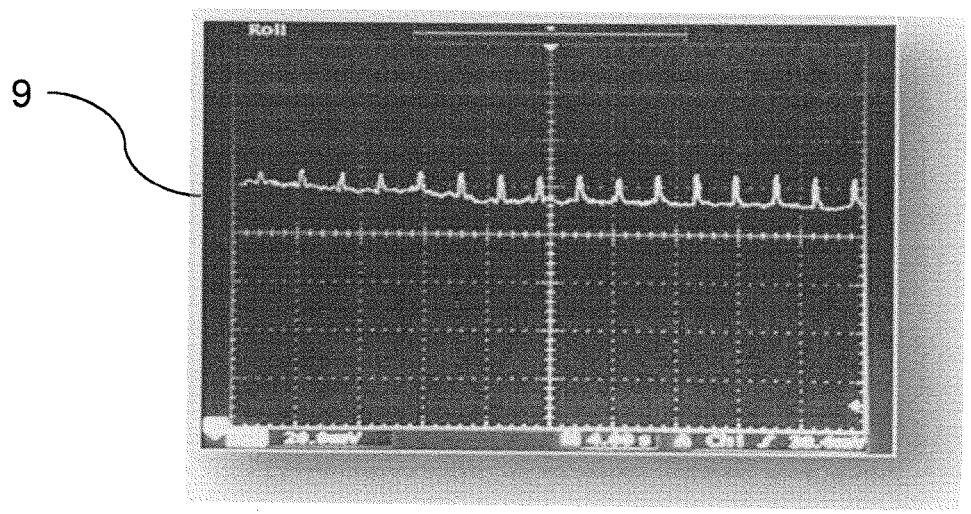
FIG. 5C a time profile of a measurement signal example.

FIG. 5C shows an example of a sample 1 in the form of a cell cluster. The cell cluster is located in a hanging drop, only a part of which can be seen in FIG. 5A, formed in a cavity of a hanging drop multi-titer plate. The sample consists of a heart muscle tissue model differentiated from stem cells, which adheres to carrier beads 15 in the form of an alginate. The sample shown in FIG. 5A has a diameter of approx. 1 millimeter.

The sample 1 is completely illuminated with light of a wavelength of 650 nm with a laser diode. The sample 1 structured on different size scales diffracts coherent light in diverse ways and generates a complex diffraction pattern (so-called "speckle pattern") in transmitted light direction. The small deformations of these structures in the tissue caused by the local heart muscle contractions lead to a change in the entire speckle pattern.

FIG. 5B shows images 17a and 17b as examples, which show two different conditions of a speckle pattern at minimal and maximal deflection of the contraction. Images 17a and 17b serve only for clarification, originate from another experiment, and do not show the speckle pattern of sample 1 of FIG. 5A. The measurement principle is however the same. A point in the edge area R of the diffraction pattern 17a, 17b is illustrated on the detector 2 by means of a spatial filter, for example the pinhole aperture 3b. The change of the pattern 17a, 17b now leads to a fluctuating light quantity let through by the pinhole aperture 3b, and therefore to a fluctuating detector signal 9, which is illustrated in FIG. 5C. The periodic fluctuation of the signal 9 equals the periodic contractions in the muscle tissue. The illustration in FIG. 5C serves only for clarification, but also shows no measurement signal measured during an illumination of the sample shown in FIG. 1A.

Although the invention has been described with reference to specific embodiment examples it is clear to a person skilled in the art that different changes may be carried out and equivalents used as replacement without leaving the scope of the invention. In addition many modifications may be carried out without leaving the associated scope. As a consequence, the invention is not limited to the disclosed embodiment examples, but should comprise all embodiment examples that fall into the scope of the enclosed patent claims. The invention in particular claims protection for the object and the characteristics of the subclaims irrespective of the referenced claims.

The invention claimed is:

1. A method for optical in vitro detection of a movement in a biological sample with a spatial extent in a form of at least one of a three-dimensional cell, a tissue culture, a cell cluster, and a sample of freely swimming microorganisms, comprising the steps:
   a) providing a receptacle for the biological sample, a light beam source, optics and a detector,
   a1) wherein the optics is configured to illuminate an entirety of the biological sample in the receptacle with radiation emanating from the light beam source and to guide at least a part of the radiation from the light beam source, which is changed in at least one of a radiation direction, a polarization state and a diffraction pattern at any point within the biological sample through interaction with the biological sample, onto a detection surface of the detector, and
   a2) wherein the detector is at least one member selected from the group consisting of: a detector that is a non-imaging detector and a detector with a non-spatially resolved measurement signal, wherein the detector is configured to generate a measurement signal depending on detected radiation, wherein a time profile of the measurement signal specifies a time profile of an intensity of the detected radiation and/or the time profile of the intensity of the detected radiation can be derived from the measurement signal;
   b) illuminating the biological sample with radiation from the light beam source;
   c) detecting a movement in the biological sample depending on a temporal change of the measurement signal, wherein
   d) the light beam source generates coherent light, and
   e) the optics is configured to map an edge area of a diffraction pattern generated by light from the light beam source that is diffracted by the biological sample, on the detector,
   f) wherein the optics comprises a pinhole aperture arranged between the biological sample and the detector in such a way that a pinhole of the pinhole aperture is arranged in the edge area of the diffraction pattern generated by the biological sample.

2. The method according to claim 1, wherein a diameter of the biological sample
   a) is at least 50 micrometers (μm) in at least one spatial direction, or
   b) lies within a range of 100 μm to 1 mm.

3. The method according to claim 1, wherein the biological sample contains at least one of living cells and cells that can trigger a movement.

4. The method according to claim 3, wherein the living cells are muscle cells.

5. The method according to claim 1, wherein at least one of a) the optics is configured and b) the detector is arranged relative to the illumination beam path and the biological sample in such a way that no beam paths exist where the radiation of the light beam source transmitted through the biological sample reaches the detector and/or where light from the light beam source reaches the detector whilst bypassing the biological sample.

6. The method according to claim 1, wherein a movement in the biological sample is detected if at least one of a change in the measurement signal exceeds a pre-determined threshold value and if the temporal change of the measurement signal has periodicity.

7. The method according to claim 1, wherein the optics comprises at least one of:
   a) an aperture arranged between the light beam source and the biological sample that is designed in such a way that radiation from the light beam source existing through an aperture opening of the aperture does not reach the pinhole of the pinhole aperture directly, and
   b) a refractive optical element, arranged between a light beam source and the biological sample, that is designed in such a way that radiation diffracted by the refractive element does not reach the pinhole of the pinhole aperture directly.

8. The method according to claim 1, wherein the optics comprises a first polarization filter and a second polarization filter, which have different polarization directions, wherein the first polarization filter is arranged between the light beam source and the biological sample and the second polarization filter between the biological sample and the detector.

9. The method according to claim 1, wherein the detector is at least one member selected from the group consisting of
   a) a detector that is arranged on a same side of the biological sample as the light beam source for the epidetection of light diffused by the biological sample;
   b) a detector that is arranged to a side of the biological sample for the detection of diffused side radiation of the biological sample with regard to the direction of the illumination beam path;
   c) a detector that is arranged in the transmitted light direction of the biological sample for the transmitted light detection of light diffused by the biological sample, and in that the optics comprises at least one of
   c1) an aperture arranged between the light beam source and the biological sample, which is designed for blocking light beams in the illumination beam path that would reach the detector as beams transmitted through the biological sample, and
   c2) a refractive element arranged between the light beam source and the biological sample, which is designed to change a direction of the illumination beam path in such a way that light beams transmitted through the biological sample will not reach the detector.

10. The method according to claim 1, wherein the optics comprises a bandpass filter arranged before the detector, which is designed for suppressing room light.

11. The method according to claim 1, wherein the receptacle for the biological sample comprises at least one of a carrier matrix and a hanging drop.

12. The method according to claim 11, wherein the receptacle for the biological sample comprises a biopolymer as a carrier matrix.

13. The method according to claim 1, wherein the receptacle for the biological sample is a cavity of a multi-well plate or a hanging drop multi-well plate.

14. The method according to claim 1, where a parallel optical detection of a movement is carried out in several biological samples that are separate from each other,
   wherein the receptacle for the biological samples is a multi-well plate or a hanging drop multi-well plate, which has a multitude of cavities for receiving biological samples, arranged in rows and columns, and
   wherein the detector is designed as a detector array, wherein a grid distance of individual detectors equals a grid distance of the cavities of the multi-well plate.

15. The method according to claim 14, wherein the detector array is a photodiode array.

16. The method according to claim 14, wherein the light beam source is designed as a laser diode array for illuminating the biological samples in the cavities, wherein a grid distance of individual laser diodes equals the grid distance of the cavities of the multi-well plate and the lenses guide the light of the laser diodes into the cavities.

17. The method according to claim 16, wherein a holder of the laser diode array is made from a heat conducting material.

18. The method according to claim 16, wherein the optics comprises a micro lens array, wherein each lens of the lens array is allocated to one of the laser diodes.

19. The method according to claim 14, wherein the light of the light beam source is coupled into individual cavities containing the biological samples for illuminating the biological samples by use of an optic fiber bundle.

20. A device for contactless in-vitro detection of a movement in a biological sample with a spatial extent in a form of at least one of a three-dimensional cell, a tissue culture, a cell cluster, and a sample of freely swimming microorganisms, comprising:
   a receptacle for the biological sample,
   a light beam source,
   a detector, and
   optics, configured to illuminate an entirety of the biological sample in the receptacle with radiation emanating from the light beam source and to guide at least a part of the radiation of the light beam source, which has been changed at any point within the biological sample through an interaction with the biological sample in at least one of a radiation direction, a polarization state and a diffraction pattern, onto a detection surface of the detector,
   wherein the detector is at least one member selected from the group consisting of: a detector that is a non-imaging detector and a detector with a non-spatially resolved measurement signal, wherein the detector is configured to generate a measurement signal depending on detected radiation, wherein a time profile of the measurement signal specifies a time profile of an intensity of the detected radiation and/or wherein the time profile of the intensity of the detected radiation can be derived from the measurement signal, wherein the device further comprises an evaluation unit, which is configured to detect a movement in the biological sample by at least one of displaying and evaluating a temporal change of the detected radiation
   wherein
      the light beam source generates coherent light, and
      the optics is configured to map an edge area of a diffraction pattern generated by light from the light beam source that is diffracted by the biological sample, on the detector
      wherein the optics comprises a pinhole aperture arranged between the biological sample and the detector in such a way that a pinhole of the pinhole aperture is arranged in the edge area of the diffraction pattern generated by the biological sample.

\* \* \* \* \*